(12) United States Patent
Kusleika et al.

(10) Patent No.: US 8,480,702 B2
(45) Date of Patent: Jul. 9, 2013

(54) CONVERTIBLE EMBOLIC PROTECTION DEVICES AND METHODS OF USE

(75) Inventors: Richard S. Kusleika, Eden Prairie, MN (US); Brooke Ren, Maple Grove, MN (US)

(73) Assignee: Covidien LP, Mansfield, MA (US)

( * ) Notice: Subject to any disclaimer, the term of this patent is extended or adjusted under 35 U.S.C. 154(b) by 1259 days.

(21) Appl. No.: 11/972,778

(22) Filed: Jan. 11, 2008

(65) Prior Publication Data

US 2008/0172084 A1 Jul. 17, 2008

Related U.S. Application Data

(60) Provisional application No. 60/879,997, filed on Jan. 11, 2007.

(51) Int. Cl.
*A61M 29/00* (2006.01)
(52) U.S. Cl.
USPC .......................................... 606/200
(58) Field of Classification Search
USPC ............... 606/104–107, 113, 127, 129, 159, 606/200; 623/1.11
See application file for complete search history.

(56) References Cited

U.S. PATENT DOCUMENTS

| 3,996,938 | A | 12/1976 | Clark, III |
| 4,921,478 | A | 5/1990 | Solano et al. |
| 5,071,407 | A | 12/1991 | Termin et al. |
| 5,152,777 | A | 10/1992 | Goldberg et al. |
| 5,462,529 | A | 10/1995 | Simpson et al. |
| 5,833,650 | A | 11/1998 | Imran |
| 6,206,868 | B1 | 3/2001 | Parodi |
| 6,245,012 | B1 | 6/2001 | Kleshinski |
| 6,325,815 | B1 | 12/2001 | Kusleika et al. |
| 6,336,934 | B1 | 1/2002 | Gilson et al. |
| 6,371,971 | B1 | 4/2002 | Tsugita et al. |
| 6,383,205 | B1 | 5/2002 | Samson et al. |
| 6,743,246 | B1 * | 6/2004 | Maahs .......................... 606/200 |
| 6,878,291 | B2 | 4/2005 | Lowe et al. |
| 6,887,257 | B2 | 5/2005 | Salahieh et al. |
| 7,066,946 | B2 | 6/2006 | Douk et al. |
| 7,169,165 | B2 | 1/2007 | Belef et al. |
| 7,740,644 | B2 | 6/2010 | Beulke et al. |
| 2001/0049517 | A1 | 12/2001 | Zadno-Azizi et al. |

(Continued)

FOREIGN PATENT DOCUMENTS

| WO | WO 99/23976 A1 | 5/1999 |
| WO | WO 03/002019 A2 | 1/2003 |
| WO | WO 03/073961 A1 | 9/2003 |

OTHER PUBLICATIONS

Jun. 26, 2008 Notification of Transmittal of the International Search Report and the Written Opinion of the International Searching Authority, or the Declaration for counterpart International Application No. PCT/US2008/050838 (14 pages).

*Primary Examiner* — S. Thomas Hughes
*Assistant Examiner* — Katherine M Shi
(74) *Attorney, Agent, or Firm* — Alana T. Bergman, Esq.

(57) ABSTRACT

An embolic protection device for removing emboli from a blood vessel in a patient's body. The device comprises a mesh element being expandable from a collapsed configuration to an expanded configuration and an elongate tubular element having a proximal opening, a distal opening, and a lumen between the proximal and distal openings. The lumen has a diameter large enough to slideably accommodate a standard guidewire. The mesh element is disposed on the elongate tubular element.

79 Claims, 4 Drawing Sheets

U.S. PATENT DOCUMENTS

| | | |
|---|---|---|
| 2002/0042626 A1* | 4/2002 | Hanson et al. .............. 606/200 |
| 2002/0042628 A1* | 4/2002 | Chin et al. ................ 606/200 |
| 2002/0055747 A1 | 5/2002 | Cano et al. |
| 2002/0188276 A1 | 12/2002 | Evans et al. |
| 2003/0144685 A1* | 7/2003 | Boyle et al. ............... 606/200 |
| 2003/0176884 A1* | 9/2003 | Berrada et al. ............. 606/200 |
| 2004/0116960 A1 | 6/2004 | Demond et al. |
| 2004/0153118 A1* | 8/2004 | Clubb et al. ............... 606/200 |
| 2005/0004597 A1* | 1/2005 | McGuckin et al. .......... 606/200 |
| 2005/0126979 A1 | 6/2005 | Lowe et al. |
| 2005/0131449 A1 | 6/2005 | Salahieh et al. |
| 2006/0004405 A1 | 1/2006 | Salahieh et al. |
| 2006/0015141 A1* | 1/2006 | Linder et al. .............. 606/200 |
| 2006/0229657 A1* | 10/2006 | Wasicek et al. ............ 606/200 |

* cited by examiner

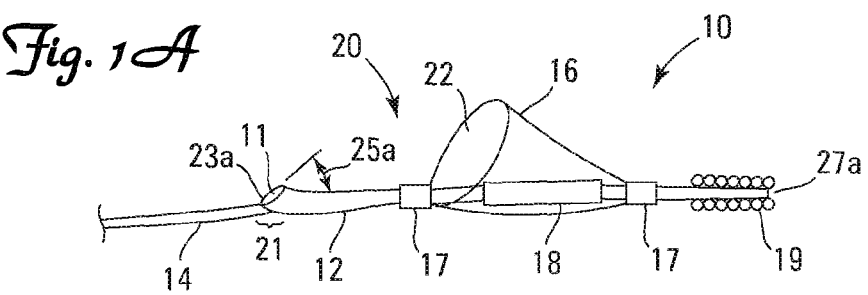
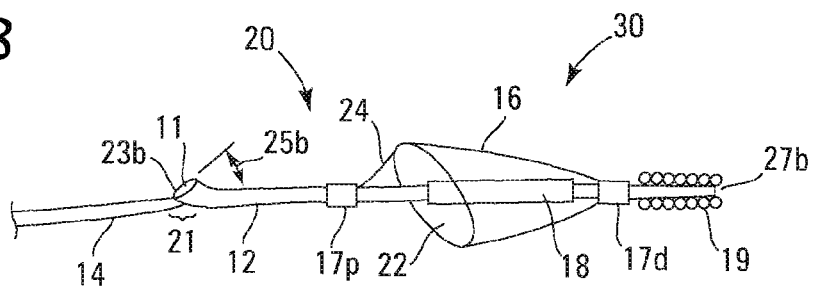
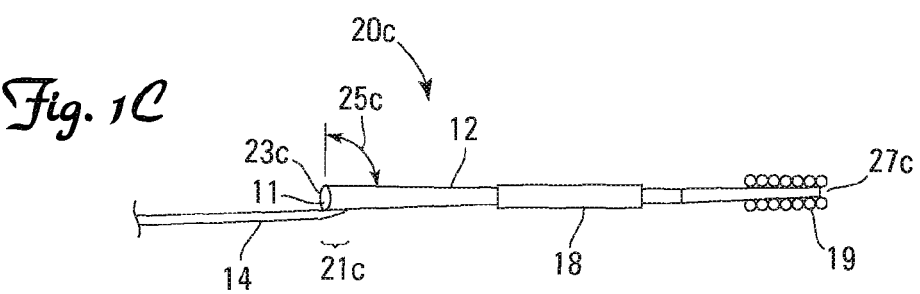
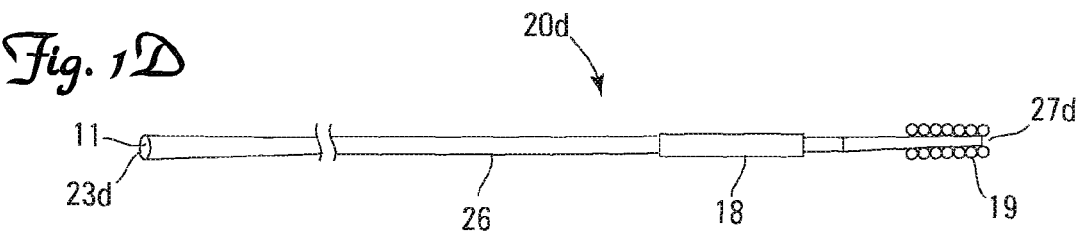

CONVERTIBLE EMBOLIC PROTECTION DEVICES AND METHODS OF USE

This application claims the benefit of U.S. Provisional Application No. 60/879,997, filed Jan. 11, 2007, entitled "Convertible Embolic Protection Devices and Methods of Use", the contents of which are hereby incorporated by reference herein.

FIELD OF THE INVENTION

The present invention relates to embolic protection systems, and, more particularly, to embolic protection systems for use in blood vessels.

BACKGROUND OF THE INVENTION

Vessels are commonly treated to reduce or eliminate narrowings caused by arteriosclerotic disease. Interventional treatments can include use of balloon angioplasty, stenting, thrombectomy, atherectomy, and other procedures. During treatment particulate debris can be generated at the treatment site. Infarcts, strokes, and other major or minor adverse events are caused when debris embolizes into vasculature from the treatment site.

To prevent embolization of debris, embolic protection devices have been developed. Embolic protection devices can remove emboli from the bloodstream by filtering debris from blood, or by occluding blood flow followed by aspiration of debris, or by causing blood flow reversal to effect removal of debris. The shape, length and other characteristics of an embolic protection device are typically chosen based on the anatomical characteristics in the vicinity of the treatment site. However, some anatomies present specific challenges due to the anatomical shape or configuration.

One type of embolic protection device is introduced into a vessel on one side of a treatment site, such as upstream from a lesion, and positioned on the other side of the treatment site, such as downstream from a lesion. Such embolic protection devices must traverse or cross the treatment site in order to be deployed in the vessel and thereby protect the patient from the effects of embolic debris. Some embolic protection devices are designed as fixed wire systems in which several components, such as a filter, a wire, and a sheath cross the treatment site in unison. However, due to the bulk of the several components not all lesions can be crossed by fixed wire embolic protection systems. Other embolic protection devices are designed to be used with wires of choice. In wire of choice systems a standard guidewire of the physician's choosing is first advanced alone across a treatment site, followed by advancement of other components, such as a filter and a sheath, over the guidewire and across the treatment site. In some cases the guidewire of choice will then be removed from the vicinity of the treatment site. While wire of choice systems are nearly 100% successful in crossing treatment sites such as lesions, they are more time consuming to use than fixed wire systems due to the added number of steps needed for initially crossing with the wire of choice and subsequently crossing with additional components.

In some anatomies fixed wire systems can be expected to cross the majority of treatment sites. Unfortunately, it is not always possible to predict which treatment sites are crossable with a fixed wire system and which treatment sites will require crossing by a wire of choice approach. If the fixed wire system cannot cross the treatment site then the system must be withdrawn and an alternate approach such as a wire of choice system must be utilized instead, increasing procedural time, complexity, and expense.

What is needed in the art is an embolic protection device that can be initially used as a fixed wire system and easily converted into a wire of choice system should the need arise.

SUMMARY OF THE INVENTION

The invention provides an embolic protection device for removing emboli from a blood vessel in a patient's body comprising a mesh element being expandable from a collapsed configuration to an expanded configuration; an elongate tubular element having a proximal opening, a distal opening, and a lumen between the proximal and distal openings, the lumen having a diameter large enough to slideably accommodate a standard guidewire; and an elongate shaft having no lumen, the elongate shaft being attached to the proximal end of the elongate tubular element. The mesh element is disposed on the elongate tubular element.

The invention provides an embolic protection device for removing emboli from a blood vessel in a patient's body, comprising a mesh element being expandable from a collapsed configuration to an expanded configuration; an elongate tubular element having a proximal end having a proximal opening, a distal end having a distal opening, and a lumen between the proximal and distal openings. The lumen has a diameter large enough to slideably accommodate a standard guidewire. The mesh element is disposed on the elongate tubular element and the mesh element is rotatable relative to the elongate tubular element when the mesh element is in the expanded configuration and no portion of the mesh element is in a fixed position relative to the elongate tubular member.

The invention provides an embolic protection device for removing emboli from a blood vessel in a patient's body comprising a mesh element being expandable from a collapsed configuration to an expanded configuration; a first elongate tubular element having a proximal end having a proximal opening, a distal end having a distal opening, and a lumen between the proximal and distal openings, the lumen having a diameter large enough to slideably accommodate a standard guidewire; a second elongate tubular element having a proximal end having a proximal opening, a distal end having a distal opening, and a lumen between the proximal and distal openings, the lumen having a diameter large enough to slideably accommodate a standard guidewire. The distal end of the second elongate tubular element is disposed in a portion of the lumen of the first elongate tubular element. A first portion of the mesh element is fixed to the first elongate tubular element and a second portion of the mesh element is fixed to the second elongate tubular element. The mesh element is expandable from a collapsed configuration to an expanded configuration by movement of the first and second elongate tubular elements relative to each other.

The invention provides a method for removing emboli from a blood vessel in a patient's body comprising providing an embolic protection device described herein and introducing the embolic protection device into a vessel in the patient's body.

According to one aspect of the present invention, an embolic protection system comprises a filter, a tubular elongate member, a sheath, and a standard guidewire. The tubular elongate member slideably receives the standard guidewire. The filter, tubular elongate member, sheath, and optionally a guidewire cooperate as a fixed wire system to cross a treatment site. If desired, the system can be converted to a wire of choice system where the guidewire initially crosses the treatment site followed by the combined filter, tubular elongate member, and sheath components. Methods of use are disclosed herein whereby the system can cross a treatment site in a patient as either a fixed wire system or as a wire of choice system.

It is to be understood that that both the foregoing general description and the following detailed description are exemplary and explanatory and are intended to provide further explanation of the invention as claimed.

BRIEF DESCRIPTION OF THE DRAWINGS

The above and further advantages of the invention may be better understood by referring to the following description in conjunction with the accompanying drawings.

FIGS. 1A and 1B illustrate conceptually side views of an embolic protection device in accordance with the present invention.

FIGS. 1C and 1D illustrate conceptually side views of a component of an embolic protection device in accordance with the present invention.

DETAILED DESCRIPTION OF THE INVENTION

Figure 2A:
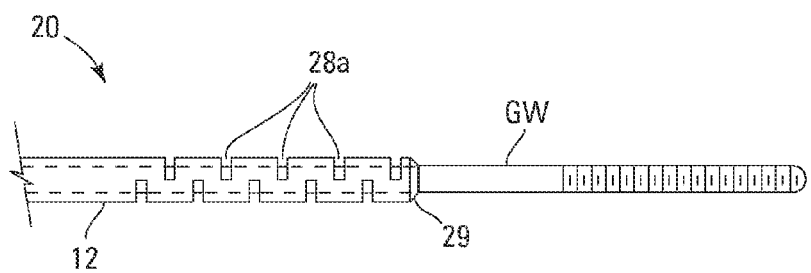
FIGS. 2A and 2B illustrate conceptually side views of a portion of an embolic protection device in accordance with the present invention.

The invention provides an embolic protection device for removing emboli from a blood vessel in a patient's body comprising a mesh element being expandable from a collapsed configuration to an expanded configuration; an elongate tubular element having a proximal end having a proximal opening, a distal end having a distal opening, and a lumen between the proximal and distal openings, the lumen having a diameter large enough to slideably accommodate a standard guidewire; and an elongate shaft having no lumen, the elongate shaft being attached to the proximal end of the elongate tubular element. The mesh element is disposed on the elongate tubular element. In one embodiment, the mesh element is rotatable relative to the elongate tubular element when the mesh element is in the expanded configuration and no portion of the mesh element is in a fixed position relative to the elongate tubular member. In an embodiment, the mesh element is slidable relative to the elongate tubular element when the mesh element is in the expanded configuration. In another embodiment, the device further comprises a guidewire disposed within the lumen of the elongate tubular element. In an embodiment, there are no stops on the guidewire.

In embodiments of the invention, the lumen has a diameter of 0.025 cm to 0.097 cm, a diameter of 0.064 cm±0.005 cm, a diameter of 0.053 cm±0.005 cm, a diameter of 0.043 cm±0.005 cm, a diameter of 0.038 cm±0.005 cm, or a diameter of 0.029 cm±0.005 cm. In embodiments of the invention, the elongate tubular element has an outer diameter of 0.030 cm to 0.100 cm, or has an outer diameter of 0.089 cm to 0.036 cm.

In one embodiment of the invention, the mesh element has an interior portion and a portion of the elongate tubular element is disposed within the interior portion. In an embodiment, the mesh element has a shape in the expanded configuration which defines an interior portion having a proximal facing opening. The mesh element can be self-expanding or self-contracting. The mesh element can be actively expanded or actively contracted.

In an embodiment of the invention, the mesh element is attached to a proximal sliding band and a distal sliding band and the sliding bands are coupled to the elongate tubular element. In one embodiment, a stop is disposed on the elongate tubular element between the proximal and distal sliding bands and the stop restricts translation of the mesh element along the elongate tubular element.

In an embodiment of the invention, the mesh element is attached to a distal sliding band and the mesh element is attached to a strut which is attached to a proximal sliding band and the sliding bands are coupled to the elongate tubular element. In one embodiment, a stop is disposed on the elongate tubular element between the proximal and distal sliding bands and the stop restricts translation of the mesh element along the elongate tubular element.

In an embodiment of the invention, the mesh element is attached to a proximal band and a distal band, the bands are coupled to the elongate tubular element, and one of the proximal and distal bands is fixed to the elongate tubular element and one of the proximal and distal bands is slidable on the elongate tubular element. In one embodiment, an actuating wire or tube is attached to the slidable band. In an embodiment, the proximal band is fixed and the distal band is slidable.

In an embodiment of the invention, the mesh element is attached to a distal band and the mesh element is attached to a strut which is attached to a proximal band, the bands are coupled to the elongate tubular element, and one of the proximal and distal bands is fixed to the elongate tubular element and one of the proximal and distal bands is slidable on the elongate tubular element. In one embodiment, an actuating wire or tube is attached to the slidable band. In an embodiment, the proximal band is fixed and the distal band is slidable.

In one embodiment, the shaft has a diameter of 0.025 cm to 0.097 cm. In an embodiment, a medical device for treatment or diagnosis is carried on the shaft. In one embodiment, the mesh element is a filter and in another embodiment the mesh element is fully occlusive.

In an embodiment, the elongate tubular element has a distal portion and a coil is disposed on the distal portion of the elongate tubular element.

In embodiments of the invention, the length of the shaft and the elongate tubular element together is from 60 cm to 320 cm, from 135 cm to 185 cm, or from 280 cm to 320 cm. In embodiments, the length of the elongate tubular element is from 5 to 75 cm or from 10 to 40 cm.

In embodiments of the invention, the mesh element expands to establish at least line contact with substantially all of a lumenal cross section of a 2 mm to 35 mm vessel or a 2 mm to 5 mm vessel.

In embodiments of the invention, the elongate tubular element has a longitudinal axis and the proximal opening of the elongate tubular element is oriented at an angle of from 5 degrees to 65 degrees to the longitudinal axis of the elongate tubular element or from 30 degrees to 105 degrees to the longitudinal axis of the elongate tubular element.

In an embodiment of the invention, the elongate tubular element has a distal end and a soft tip is attached to the distal end of the elongate tubular element. In embodiments of the invention, the elongate tubular element has a distal region that comprises slots or has a distal region that comprises removed regions. In embodiments of the invention, the elongate tubular element has a distal region that comprises a coil tip or the elongate tubular element has a distal region that comprises a composite tip.

In an embodiment of the invention, the device further comprises a sheath disposed over a portion of the mesh element. In an embodiment, the sheath comprises a proximal shaft and a tubular portion having a lumen. In another embodiment, the sheath comprises a proximal hub and a tubular portion having a lumen. In an embodiment, the sheath comprises a proximal shaft and a tubular portion having a lumen and a skive. In an embodiment, the sheath comprises a proximal shaft and a tubular portion having a lumen and two skives.

In embodiments of the invention, the mesh element is a filter and the filter comprises braided metal strands or a polymer film with holes.

The invention provides an embolic protection device for removing emboli from a blood vessel in a patient's body comprising a mesh element being expandable from a collapsed configuration to an expanded configuration; and an elongate tubular element having a proximal end having a proximal opening, a distal end having a distal opening, and a lumen between the proximal and distal openings, the lumen having a diameter large enough to slideably accommodate a standard guidewire. The mesh element is disposed on the elongate tubular element and the mesh element is rotatable relative to the elongate tubular element when the mesh element is in the expanded configuration, and no portion of the mesh element is in a fixed position relative to the elongate tubular member. In an embodiment, the mesh element is slidable relative to the elongate tubular element when the mesh element is in the expanded configuration. In one embodiment, the length of the elongate tubular element is from 60 to 320 cm. In an embodiment, the device further comprises a guidewire disposed within the lumen of the elongate tubular element. In one embodiment, the lumen has a diameter of 0.025 cm to 0.097 cm. The mesh element can be a filter or can be fully occlusive.

The invention provides an embolic protection device for removing emboli from a blood vessel in a patient's body comprising a mesh element being expandable from a collapsed configuration to an expanded configuration; a first elongate tubular element having a proximal end having a proximal opening, a distal end having a distal opening, and a lumen between the proximal and distal openings, the lumen having a diameter large enough to slideably accommodate a standard guidewire; and a second elongate tubular element having a proximal end having a proximal opening, a distal end having a distal opening, and a lumen between the proximal and distal openings, the lumen having a diameter large enough to slideably accommodate a standard guidewire. A distal region including the distal end of the second elongate tubular element is disposed in a portion of the lumen of the first elongate tubular element. A first portion of the mesh element is fixed to the first elongate tubular element and a second portion of the mesh element is fixed to the second elongate tubular element. The mesh element is expandable from a collapsed configuration to an expanded configuration by movement of the first and second elongate tubular elements relative to each other. The mesh element can be expandable from a collapsed configuration to an expanded configuration by axial or rotational movement of the first and second elongate tubular elements relative to each other. In an embodiment, the length of the device is from 60 to 320 cm. In one embodiment, the device further comprises a guidewire disposed within the lumens of the first and second elongate tubular elements. In an embodiment, the lumens of the first and second elongate tubular elements each independently have diameters of 0.025 cm to 0.097 cm. The mesh element can be a filter or can be fully occlusive.

The invention provides a method for removing emboli from a blood vessel in a patient's body comprising providing an embolic protection device and introducing the embolic protection device into a vessel in the patient's body. The embolic protection device comprises a mesh element being expandable from a collapsed configuration to an expanded configuration; an elongate tubular element having a proximal end having a proximal opening, a distal end having a distal opening, and a lumen between the proximal and distal openings, the lumen having a diameter large enough to slideably accommodate a standard guidewire; and an elongate shaft having no lumen, the elongate shaft being attached to the proximal end of the elongate tubular element, and the mesh element being disposed on the elongate tubular element. In an embodiment, the method further comprises advancing the embolic protection device through the vessel until the mesh element is positioned at a desired location distal to a treatment site and deploying the mesh element to its expanded configuration. In an embodiment, the device further comprises a guidewire disposed within the lumen of the elongate tubular element. In one embodiment, the lumen has a diameter of 0.025 cm to 0.097 cm. In an embodiment, the device further comprises a sheath disposed over a portion of the mesh element. In an embodiment, the method further comprises advancing the embolic protection device through the vessel until the mesh element is positioned at a desired location distal to a treatment site and deploying the mesh element to its expanded configuration by removing the sheath from the mesh element. In an embodiment, a guide catheter or guide lumen is advanced into the vessel in the patient's body to assist in introducing the embolic protection device. In an embodiment, a recovery catheter is used to recover the embolic protection device. In one embodiment, the guidewire is removed and replaced with a second guidewire. In an embodiment, the method further comprises advancing a medical device for diagnosis or treatment over the shaft.

In the description below the invention is described using, as examples, filters comprised of braided metal strands. It is to be understood that the invention is not limited to the examples below. For example, the mesh of the invention can be comprised of strands that are woven, non-woven, or knitted to form the mesh, or some other structure that prevents the travel of embolic material. The mesh can have uniform strand spacing so as to define a structure with relatively uniformly sized openings between strands or can have variable strand spacing so as to define a structure with varied size openings between strands. The mesh can be coated with an elastic polymer film in whole or in part, or with another material, so as to reduce in size or eliminate the openings between strands. The coated or uncoated mesh may be partially or totally occlusive to flow of fluid or particles therethrough. In some embodiments the metal strands may be superelastic alloys comprised of radiopaque alloy constituents. In some preferred embodiments one or more metal strands are comprised of nickel-titanium-platinum or nickel-titanium-tantalum alloy. In addition, some or all of the strands may be comprised of materials other than metal including but not limited to engineering polymers such as polyetheretherketone (PEEK), liquid crystal, polyamide, or polyester; ceramics; glass-ceramics; metallic glasses; or other materials known in the art. In some embodiments the aforementioned materials can be comprised of radiopaque filler materials. It is further understood that the cross section of some or all of the strands can be round, ovoid, square, rectangular, triangular, irregular, symmetrical, non-symmetrical, or other shapes.

In another aspect of the invention the mesh can be comprised of a polymer film with holes produced by laser drilling, casting followed by dissolution of substances such as salts (leaving holes where the salt was dissolved), casting or forming into molds, or other methods as are known in the art. The mesh may be supported in whole or in part by struts comprised of metal, polymer, ceramic, metallic glass, or other materials. The struts may be aligned along the longitudinal axis of the embolic protective device, transverse to the longitudinal axis of the device, a combination of the two, or other orientations.

In the description below the invention is further described using as examples a generally conical shape embolic protective device with a proximal facing opening. It is to be understood that the invention is not limited to the examples below. For example, the embolic protective device of the invention can have a variety of other shapes such as generally cylindrical, cup shaped, generally planar, or any other shape and may have a distally facing opening, proximal and distal openings, an opening off axis from the central longitudinal axis of the device, a sidewall opening, and no opening at all. The embolic protective device may be self-expanding, that is, have a tendency to radially or longitudinally expand, or both, when unconstrained; may be self-contracting, be partially both self-expanding and self-contracting, or may have no tendency to either expand or contract when not constrained. The embolic protective device may also be actively actuated radially or longitudinally or both by attaching a proximal end and a distal end of the device to telescoping structures, by using an inflatable structure such as a balloon to expand and contract the device, or by using other methods, as is known in the art. Additionally, it is contemplated that the embolic protection device prevents the travel of embolic material distal of the embolic protection device through the above-recited concepts, and provided by other materials, shapes and structures not disclosed herein, but that provide the same functions.

It is understood that the radiopaque elements discussed below can be comprised of a range of radiopaque materials known in the art. Materials such as platinum, rhenium, iridium, tungsten, gold, lead, barium sulphate, bismuth oxychloride, bismuth subcarbonate, lead oxide, iodine containing compounds, barium containing compounds, ceramics, metallic glasses, and others may be used. Various physical forms comprised of radiopaque materials can be prepared and applied to embolic protective devices, such as monofilament wires, composite wires, stranded wires, cables, sheet, strip, mesh, sponge, sintered powders, powders or fibers embedded into matrices such as polymer matrices, tubes, and other forms.

FIG. 1A illustrates convertible embolic protection device 10 comprised of host wire 20, mesh 16, and sliding bands 17. Host wire 20 is comprised of elongate tubular member 12, shaft 14, stop 18, and coil 19. Elongate tubular member 12 may be comprised of strong, flexible, and kink resistant material such as thin walled polyimide tubing reinforced with braided nitinol flat wire and has an inside diameter large enough to slideably accommodate a standard guidewire (not shown). Elongate tubular member 12 has proximal opening 23a oriented at angle 25a to the longitudinal axis of elongate tubular member 12 and distal opening 27a. Lumen 11 connects the proximal opening 23a and the distal opening 27a. Angle 25a may range from 5 degrees to 65 degrees, from 10 degrees to 45 degrees, or from 15 degrees to 30 degrees in various embodiments. Shaft 14 may be comprised of solid metal wire such as nitinol or stainless steel and in some embodiments has mechanical properties similar to those of a standard guidewire shaft such that medical devices for treatment and diagnosis can be exchanged over shaft 14. Exemplary medical devices for treatment and diagnosis include but are not limited to angioplasty catheters, stent delivery catheters comprised of stents, atherectomy catheters, thrombectomy catheters, aspiration catheters, injection catheters, ultrasonic diagnosis catheters, angiography catheters, and the like. Elongate tubular member 12 and shaft 14 are joined at region 21 by means of welding, adhesives, mechanical interlock, or other means known in the art. Mesh 16 is comprised any of the materials listed above and has opening 22. For clarity mesh 16 is represented by an outline in the figures and pores or openings in the mesh (if present) are not shown. In one embodiment, mesh 16 is comprised of 48 circular cross section monofilament nitinol wires braided together in a 2 over 2 braiding pattern heat set in molds to have self-expanding characteristics. Sliding bands 17 may be comprised of radiopaque materials such as platinum and are attached to mesh 16 by welding, adhesives, mechanical interlock, or other means. In one embodiment the distal end of distal sliding band 17 is tapered to form a smooth transition in diameter between the outer diameter of elongate tubular member 12 and the outer diameter of distal most band 17. In embolic protection device 10 the center of opening 22 in mesh 16 is offset from the axis of elongate tubular member 12. In another embodiment the center of opening 22 in mesh 16 is not offset from the axis of elongate tubular member 12. Sliding bands 17 each have a lumen (not shown) and elongate tubular member 12 is rotatably and axially slideably accommodated in the lumen of bands 17. Stop 18 is made of metal, polymer, ceramic, or combinations of these materials, including stainless steels, shape memory materials, superelastic materials, PEEK, polyimide, polyester, ELGILOY® alloy, polyether block amide such as PEBAX® polymer, gold, platinum and its alloys, and other materials as are known in the art. Stop 18 is permanently affixed to elongate tubular member 12 by welding, brazing, soldering, adhesives, mechanical interlock, or other means and may be comprised of slots, slits, spiral cuts, holes, reduced thickness regions, annealed regions, or other geometry to improve the lateral flexibility of stop 18. In one embodiment (not shown) stop 18 is comprised of two rings of material separated by a distance. In another embodiment stop 18 also functions as a connector to join an elongate tubular member 12 comprised of distinct proximal and distal portions (not shown). The outer diameter of stop 18 is large enough to prevent bands 17 from sliding over stop 18. Coil 19 may be comprised of monofilament, stranded, or cable wire wound in a coil geometry and may be comprised of radiopaque materials such as gold, tungsten, or other materials known in the art. In one embodiment both ends of coil 19 are attached to a distal region of elongate tubular member 12 by welding, adhesives, mechanical interlock, or other means. Further description of a filter similar to that illustrated in FIG. 1A is disclosed in U.S. Pat. No. 6,325,815 B1 to Kusleika et al., entitled "Temporary Vascular Filter", the contents of which are incorporated herein by reference.

In some embodiments of convertible embolic protection device 10, host wire 20 ranges in length from 60 cm to 320 cm. In one embodiment host wire 20 ranges in length from 135 cm to 185 cm and in another embodiment host wire 20 ranges in length from 280 cm to 320 cm. In some embodiments of convertible embolic protection device 10, elongate tubular member 12 ranges in length from 5 cm to 75 cm. In one embodiment elongate tubular member 12 ranges in length from 10 cm to 40 cm and in another embodiment elongate tubular member 12 ranges in length from 15 cm to 25 cm.

In some embodiments of convertible embolic protection device 10, elongate tubular member 12 slideably accommodates guidewires having diameters of either 0.010" (0.025 cm) diameter, 0.014" (0.036 cm) diameter or less, 0.018" (0.046 cm) diameter or less, 0.021" (0.053 cm) diameter or less, 0.035" (0.089 cm) diameter or less, or 0.038" (0.097 cm) diameter or less. In some embodiments of convertible embolic protection device 10, the shaft 14 has diameters of either 0.010" (0.025 cm) diameter, 0.014" (0.036 cm) diameter or less, 0.018" (0.046 cm) diameter or less, 0.021" (0.053 cm) diameter or less, 0.035" (0.089 cm) diameter or less, or 0.038" (0.097 cm) diameter or less. In some embodiments of convertible embolic protection device 10, mesh 16 expands to establish at least line contact with substantially all of a lumenal cross section of a 2 mm to 35 mm vessel. In one embodiment, mesh 16 expands to establish at least line contact with substantially all of a lumenal cross section of a 2 mm to 5 mm vessel, and in another embodiment mesh 16 expands to establish at least line contact with substantially all of a lumenal cross section of a 4 mm to 7 mm vessel. In another embodiment, mesh 16 expands to establish at least line contact with substantially all of a lumenal cross section of a 6 mm to 12 mm vessel. In another embodiment, mesh 16 expands to establish at least line contact with substantially all of a lumenal cross section of a 10 mm to 20 mm vessel, and in another embodiment mesh 16 expands to establish at least line contact with substantially all of a lumenal cross section of a 20 mm to 30 mm vessel.

FIG. 1B illustrates convertible embolic protection device 30 comprised of host wire 20, mesh 16, sliding bands 17p and 17d, and strut 24. Host wire 20 is comprised of elongate tubular member 12, shaft 14, stop 18, and coil 19. Host wire 20, elongate tubular member 12 with opening 23b having angle 25b and distal opening 27b, lumen 11, shaft 14, mesh 16 with opening 22, stop 18, and coil 19 have substantially the same construction, dimensions, and function as those described above in conjunction with FIG. 1A. One or more struts 24 connect sliding band 17p and mesh 16, and may be comprised of monofilament, stranded, or cabled metal wire, thread, polymer strand, suture, axially oriented polymer film, or other materials. Sliding bands 17p and 17d in one embodiment are comprised of radiopaque materials such as platinum. Sliding band 17d is attached to mesh 16 by welding, adhesives, mechanical interlock, or other means. Sliding band 17p is attached to one or more struts 24 by welding, adhesives, mechanical interlock, or other means. In embolic protection device 30, the center of opening 22 in mesh 16 can be coincident with axis of elongate tubular member 12 or can be offset from axis of elongate tubular member 12. Sliding bands 17p and 17d have lumens (not shown) and elongate tubular member 12 may be rotatably and axially slideably accommodated in lumen of bands 17p and 17d.

In an alternate embodiment of devices 10, 30 one of sliding bands 17, 17p, 17d is fixed to tubular member 12 and the second band 17, 17p, 17d is free to slide over tubular member 12. In some embodiments the proximal band 17, 17p, is fixed to tubular member 12 and the distal band 17, 17d is free to slide over tubular member 12. In yet another embodiment of devices 10, 30 an actuating wire or tube is parallel to shaft 14 and attached to at least one slideable band such that mesh 16 can be actively collapsed or expanded by moving the actuating wire or tube relative to shaft 14.

FIGS. 1C and 1D illustrate alternative versions of host wire 20. In FIG. 1C host wire 20c is comprised of elongate tubular member 12, shaft 14, stop 18, and coil 19. Elongate tubular member 12, shaft 14, stop 18, and coil 19 have substantially the same construction, dimensions, and function as those described above in conjunction with FIG. 1A. Elongate tubular member 12 has opening 23c oriented at angle 25c ranging from 30 degrees to 105 degrees, from 35 degrees to 90 degrees, or from 40 degrees to 75 degrees, and has distal opening 27c. Lumen 11 connects the proximal opening 23c to the distal opening 27c. Shaft 14 is attached to outer wall of elongate tubular member 12 in region 21c so as to not impede the sliding motion of guidewire (not shown) in the lumen of elongate tubular member 12.

In FIG. 1D host wire 20d is comprised of elongate tubular member 26, stop 18, and coil 19. Stop 18 and coil 19 have substantially the same construction, dimensions, and function as those described above in conjunction with FIG. 1A. Elongate tubular member 26 may be comprised of strong, flexible, and kink resistant material such as thin walled polyimide tubing reinforced with braided nitinol flat wire and has an inside diameter large enough to slideably accommodate a standard guidewire (not shown). Elongate tubular member 26 has proximal opening 23d and distal opening 27d and has mechanical properties similar to those of a standard guidewire shaft such that medical devices for treatment and diagnosis can be exchanged over elongate tubular member 26. Lumen 11 connects the proximal opening 23d to the distal opening 27d. Exemplary medical devices for treatment and diagnosis include but are not limited to angioplasty catheters, stent delivery catheters comprised of stents, atherectomy catheters, thrombectomy catheters, aspiration catheters, injection catheters, ultrasonic diagnosis catheters, angiography catheters, and the like. In some embodiments host wire 20d ranges in length from 60 cm to 320 cm. In one embodiment host wire 20d ranges in length from 135 cm to 185 cm and in another embodiment host wire 20d ranges in length from 280 cm to 320 cm. In some embodiments elongate tubular member 26 slideably accommodates guidewires having diameters of either 0.010" (0.025 cm) diameter, 0.014" (0.036 cm) diameter or less, 0.018" (0.046 cm) diameter or less, 0.021" (0.053 cm) diameter or less, 0.035" (0.089 cm) diameter or less, or 0.038" (0.097 cm) diameter or less.

In one embodiment elongate tubular member 26 has an outside diameter of 0.035" (0.089 cm) and an inside diameter within the range of 0.025"±0.002" (0.064 cm±0.005 cm). In another embodiment elongate tubular member 26 has an outside diameter of 0.035" (0.089 cm) and an inside diameter within the range of 0.021"±0.002" (0.053 cm±0.005 cm). In another embodiment elongate tubular member 26 has an outside diameter of 0.035" (0.089 cm) and an inside diameter within the range of 0.017"±0.002" (0.043 cm±0.005 cm). In another embodiment elongate tubular member 26 has an outside diameter of 0.018" (0.046 cm) and an inside diameter within the range of 0.015"±0.002" (0.038 cm±0.005 cm). In another embodiment elongate tubular member 26 has an outside diameter of 0.014" (0.036 cm) and an inside diameter within the range of 0.0115"+0.001" (0.029 cm±0.0025 cm). In one embodiment, the elongate tubular member has an inside diameter of 0.025 cm to 0.097 cm. In one embodiment, the elongate tubular member has an outside diameter of 0.030 cm to 0.100 cm and in another embodiment the elongate tubular member has an outside diameter of 0.089 to 0.036 cm.

In an alternate embodiment elongate tubular member 26 is comprised of telescoping tubes (not shown). One of sliding bands 17, 17p, 17d is fixed to the inner telescoping tube and the second band 17, 17p, 17d is fixed to the outer telescoping tube, such that mesh 16 can be actively collapsed or expanded by moving the telescoping tubes axially or rotationally relative to each other.

Figure 2B:
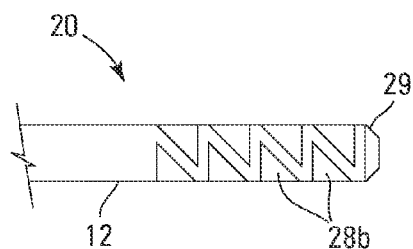

FIGS. 2A and 2B describe further embodiments of host wire 20. While the embodiments of FIGS. 2A and 2B are described in relation to host wire 20 it is contemplated that these embodiments can also be applied to host wires 20c and 20d. Distal region of host wire 20 in FIG. 2A is comprised of elongate tubular member 12 (or 26 in the case of host wire 20d), slots 28a, and soft tip 29. Slots 28a serve to increase the bending flexibility of host wire 20 and may vary in number, width, depth, and orientation relative to axis of elongate tubular member. Slots 28a may remove part or all of the thickness of the elongate tubular member. Similarly, regions 28b in FIG. 2B are removed from elongate tubular member 12 (or 26 in the case of host wire 20d) to increase the bending flexibility of host wire 20 and may vary in number, width, depth, area, shape, and orientation relative to axis of elongate tubular member. Slots or regions may be formed into host wire 20 by grinding, laser cutting, etching, punching, or other means as are known by those skilled in the art.

Soft tip 29 is attached to distal end of elongate tubular member 12 (or 26 in the case of host wire 20d) and may be comprised of polymers such as polyether block amide (for example PEBAX®), silicone, styrene-ethylene-butylene-styrene block copolymer (for example C-FLEX®), rubber, or other polymers. Soft tip 29 prevents the distal end of the elongate tubular member from damaging the internal surface of a conduit such as a vessel. Soft tip 29 also provides a smooth transition between standard guidewire GW (shown in FIG. 2A) and the elongate tubular member by having an inside diameter approximately equal to the outside diameter of guidewire GW, an outside diameter approximately equal to the outside diameter of elongate tubular member, and a gradual transition between these two diameters.

Figure 3A:
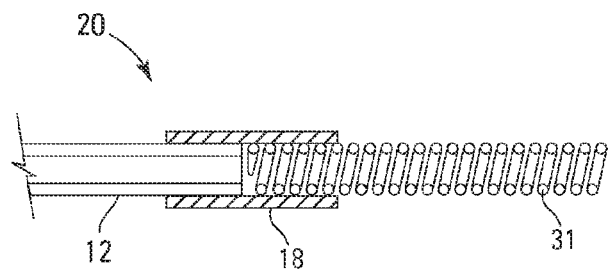
FIGS. 3A and 3B illustrate conceptually cross sectional views of a portion of an embolic protection device in accordance with the present invention.
Figure 3B:
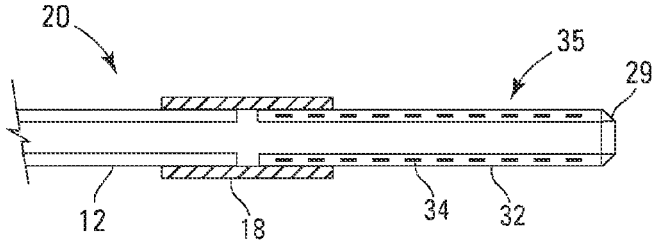

FIGS. 3A and 3B describe further embodiments of host wire 20. While the embodiments of FIGS. 3A and 3B are described in relation to host wire 20 it is contemplated that these embodiments can be applied to host wires 20c and 20d. Distal region of host wire 20 in FIG. 3A is comprised of elongate tubular member 12 (or 26 in the case of host wire 20d), stop 18, and coil tip 31. Coil tip 31 and elongate tubular member 12 are attached to stop 18 by means of adhesive, welding, brazing, soldering, crimping, or other means known by those skilled in the art. Coil tip 31 provides a flexible terminus to host wire 20 and may be comprised of metallic wire such as nitinol, gold, platinum, or other metals, and may be radiopaque. Coil tip 31 may be coated with polymer coverings (not shown) and in some embodiments a safety wire (not shown) maintains the distance between at least two points along the length of coil tip 31.

Distal region of host wire 20 in FIG. 3B is comprised of elongate tubular member 12 (or 26 in the case of host wire 20d), stop 18, and composite tip 35. Composite tip 35 is comprised of polymer matrix 32, reinforcement 34 and soft tip 29. Composite tip 35 and the elongate tubular member are attached to stop 18 by means of adhesive, welding, brazing, soldering, crimping, or other means known by those skilled in the art. Composite tip 35 provides a flexible terminus to host wire 20. Polymer matrix 32 may be comprised of polyimide, polyether block amide such as PEBAX®, polyester, nylon, or other materials, may be comprised of two or more layers in thickness, and may be comprised of different materials along the length of the composite tip. Reinforcement 34 may be comprised of braided, woven, coiled, or other material forms, may be comprised of metallic wire such as nitinol, gold, platinum, or other metals, may be radiopaque, or may be comprised of polymer wire, ribbon, or other material forms.

Figure 4:
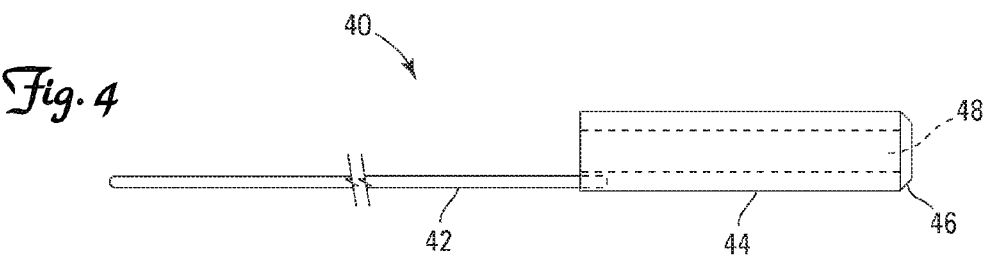
FIGS. 4 and 5 illustrate conceptually side views of sheaths in accordance with the present invention.

FIG. 4 illustrates sheath 40 usable with embolic protection devices 10 and 30. Sheath 40 is comprised of shaft 42, tubular portion 44, and soft tip 46. Shaft 42 and soft tip 46 are attached to tubular portion 44 by molding, fusing, welding, adhesives, bonding, or other means as are known to those of skill in the art. Shaft 42 is comprised of metal or stiff polymer such as stainless steel, nitinol, polyimide, nylon, or other materials and in some embodiments ranges in length from 120 cm to 180 cm. Tubular portion 44 is comprised of polymer such as nylon, polyether block amide (for example PEBAX®), polyethylene, polyester, polybutylene terephthalate-long chain polyether glycols block copolymer (for example HYTREL®), PEEK, polyimide, braid reinforcement, metal reinforcement, or other materials, and in some embodiments ranges in length from 10 cm to 40 cm. Tubular portion 44 has lumen 48 which slideably receives embolic protection devices 10 and 30. Soft tip 46 may be comprised of polymers such as polyether block amide (for example PEBAX®), silicone, styrene-ethylene-butylene-styrene block copolymer (for example C-FLEX®), rubber, or other polymers. Soft tip 46 prevents distal end of tubular portion 44 from damaging the internal surface of a conduit such as a vessel. Soft tip 46 also provides a smooth transition between embolic protection devices 10 and 30 and tubular portion 44 by having an inside diameter approximately equal to the outside diameter of band 17 or 17d, an outside diameter approximately equal to the outside diameter of tubular portion 44, and a gradual transition between these two diameters (see FIG. 8).

Figure 5:
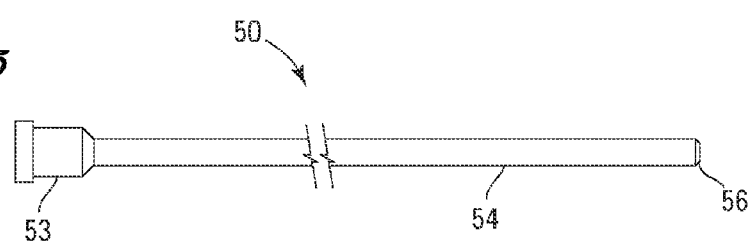

FIG. 5 illustrates sheath 50 usable with embolic protection devices 10 and 30. Sheath 50 is comprised of hub 53, tubular portion 54, and soft tip 56. Hub 53 is comprised of polycarbonate or other materials known in the art and standardized luer fitting geometry that is compatible with interconnecting components such as syringes. Tubular portion 54 and soft tip 56 have substantially the same construction, dimensions, and function as those described above in conjunction with FIG. 4 for tubular portion 44 and soft tip 46. In some embodiments sheath 50 ranges in length from 60 cm to 180 cm. In some embodiments sheath 50 ranges in length from 160 cm to 180 cm, or from 250 cm to 320 cm.

Figure 6:
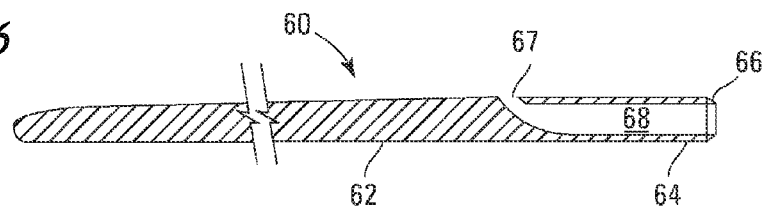
FIGS. 6 and 7 illustrate conceptually cross sectional views of sheaths in accordance with the present invention.

FIG. 6 illustrates sheath 60 usable with embolic protection devices 10 and 30. Sheath 60 is comprised of shaft 62, tubular portion 64 having lumen 68 and skive 67, and soft tip 66. Shaft 62, tubular portion 64 and soft tip 66 have substantially the same construction, dimensions, and function as those described above in conjunction with FIG. 4 for shaft 42, tubular portion 44 and soft tip 46. Skive 67 comprises a passageway through the sidewall of tubular portion 64 between the lumen 68 of tubular portion 64 and the outside diameter of tubular portion 64. In one embodiment skive 67 is dimensioned to allow passage therethrough of shaft 14, guidewire GW, or elongated tubular member 26. In another embodiment skive 67 is dimensioned to allow passage therethrough of shaft 14 and guidewire GW simultaneously. In another embodiment skive 67 is dimensioned to allow passage therethrough of elongated tubular member 26 and guidewire GW simultaneously.

Figure 7:
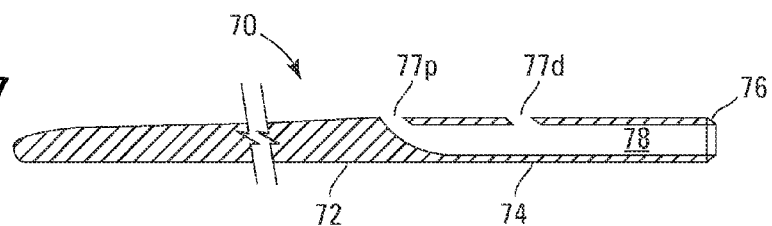

FIG. 7 illustrates sheath 70 usable with embolic protection devices 10 and 30. Sheath 70 is comprised of shaft 72, tubular portion 74 having lumen 78 and two skives 77p and 77d, and soft tip 76. Shaft 72, tubular portion 74 and soft tip 76 have substantially the same construction, dimensions, and function as those described above in conjunction with FIG. 4 for shaft 42, tubular portion 44 and soft tip 46. Skives 77p and 77d have substantially the same construction, dimensions, and function as those described above in conjunction with FIG. 6 for skive 67.

In some embodiments, any of sheaths 40, 50, 60, or 70, shafts 14, or elongate tubular member 26 can be locked together to preserve the axial relationship of one relative to another, for example, by means of a compression fitting such as a Tuohy-Borst adaptor, or other means as are known to those of skill in the art.

An exemplary method of using a convertible embolic protection device in accordance with the present invention is now described. A guide catheter or sheath (not shown) is used to access a vessel proximal to a lesion L in a patient using methods known in the art. A standard guidewire GW is chosen based on evaluation of lesion L and guidewire GW is backloaded through lumen 11 of tubular member 12 or 26 leaving tip of guidewire GW extending distal to the tubular member as illustrated in FIG. 8.

Figure 8:
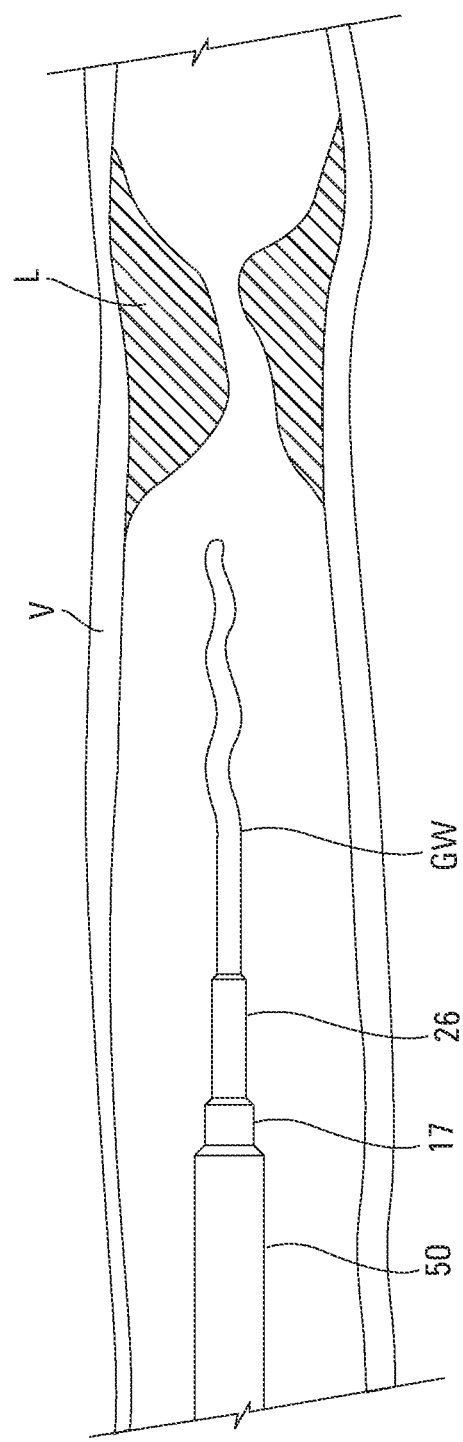
FIG. 8 illustrates conceptually a partial sectional view of an embolic protection system in a vessel in accordance with the present invention.

Embolic protection device 10 or 30 containing guidewire GW is backloaded into sheath 40, 50, 60, or 70 and positioned such that distal most sliding band 17 or 17d is partially exposed beyond the distal end of the sheath as illustrated in FIG. 8. The sheath/device/guidewire combination is advanced through a guide catheter or guide sheath as a fixed wire system to the vicinity of treatment site such as lesion L. The sheath/device/guidewire combination is then advanced across lesion L. In the event that the sheath/device/guidewire combination cannot be advanced across lesion L, the components are subsequently used as a wire of choice system, in which guidewire GW alone is advanced across the lesion followed by advancement of the sheath/device combination.

The sheath is then withdrawn to allow mesh 16 to expand or be expanded into contact with vessel V. Sheath and guidewire GW are thereafter withdrawn from the patient. The treatment site is then diagnosed, treated, or both by advancing diagnostic or treatment devices or both along shaft 14 of the embolic protection device or along elongate tubular member 26 of the embolic protection device. For example balloon angioplasty, atherectomy, or stent catheters may be advanced and used to effect treatment before being withdrawn. Emboli liberated by the diagnostic or treatment devices are captured by embolic protection device 10, 30.

Embolic protection device 10, 30 with captured emboli therein is then recovered using a suitable recovery catheter. The recovery catheter may be advanced to cover at least a portion of the embolic protection device 10, 30 with captured emboli, or the embolic protection device 10, 30 with captured emboli may be drawn at least partially into the recovery catheter, after which the device/recovery catheter combination is withdrawn from the patient.

In the event that embolic protection device 10 or 30 containing guidewire GW is backloaded into sheath 60 then each of shaft 14, elongate tubular member 26, and guidewire GW (to the extent they are used) will pass through skive 67. In the event that embolic protection device 10 or 30 containing guidewire GW is backloaded into sheath 70 then shaft 14 will pass through skive 77p and guidewire GW will pass through skive 77d or elongate tubular member 26/guidewire GW combination will pass through either of skive 77p or 77d.

In addition to the advantages described above, guidewires can be backloaded into embolic protection device 10 or 30 without guidewire GW damaging the filter and without obstruction of guidewire passage during backloading. This is the case because elongate tubular members 12, 26 provide a dedicated passageway for guidewire GW. In some methods embolic protection device 10 or 30 is backloaded into sheath 40, 50, 60, or 70 prior to backloading guidewire GW. In some embodiments embolic protection device 10 or 30 is preloaded in a sheath when shipped for easy priming and fewer steps during the treatment procedure and associated preparation.

In an alternative method to that described above, a guidewire GW is not used and the embolic protection device 10 or 30/sheath combination is advanced across the lesion as a fixed wire system without conversion of the system to a wire of choice system. In yet another alternative method to that described above, a device that can be actively expanded or contracted is used and use of a sheath is optional.

Embolic protection devices 10 or 30 comprised of elongate tubular member 26 offer several advantages in addition to those described above. In one method, after conversion to a wire of choice system, guidewire GW can be replaced with a different guidewire of choice. This can be very helpful when the guidewire in use becomes damaged or is otherwise unsuitable for crossing lesion L. To replace guidewire GW with a different guidewire of choice, guidewire GW is withdrawn from the patient and the different guidewire is frontloaded into proximal opening 23d of elongate tubular member 26 and advanced though elongate tubular member 26 to the vicinity of the lesion.

In another method, a guidewire GW is not used initially and the physician attempts to advance across the lesion the embolic protection device 10 or 30 having elongate tubular member 26 and sheath combination as a fixed wire system. In the event that the lesion cannot be crossed as a fixed wire system, conversion of the system to a wire of choice system is possible by frontloading a guidewire GW into proximal opening 23d of elongate tubular member 26 and advancing the guidewire though elongate tubular member 26 to the vicinity of the lesion. In yet another alternative method to that described above, a device that can be actively expanded or contracted is used and use of a sheath is optional.

In another method, a physician can alter the stiffness of elongate tubular member 26 during a procedure by positioning a guidewire within, or removing a guidewire from, or changing the characteristics of a guidewire within the lumen of the elongate tubular member.

In yet another method, after treatment, diagnosis, or both, one can leave guidewire GW in place within the vessel or across the lesion and remove embolic protection device 10 or 30 by withdrawing elongate tubular member 26 from guidewire GW. In some embodiments, guidewire GW will be an exchange length guidewire to facilitate withdrawing of elongate tubular member 26 from guidewire GW. In some cases it is helpful to observe a treatment site after treatment while preserving guidewire access to the treatment site in the event that further intervention becomes warranted.

While this document has described an invention mainly in relation to embolic protection devices used in vessels, it is envisioned that the invention can be applied to other conduits in the body as well including veins, bronchi, ducts, ureters, urethra, and other lumens intended for the passage of air, fluids, or solids. The invention can be applied to other devices such as vena cava filters, stents, septal defect closure devices, intracranial filters, aneurism excluders, and other devices comprised of mesh having the benefits described above.

While the various embodiments of the present invention have related to embolic protection filtering devices, the scope of the present invention is not so limited. Further, while choices for materials and configurations have been described above with respect to certain embodiments, one of ordinary skill in the art will understand that the materials described and configurations are applicable across the embodiments.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. An embolic protection device for removing emboli from a blood vessel in a patient's body, comprising:
   a mesh element being expandable from a collapsed configuration to an expanded configuration;
   an elongate tubular element having a proximal end having a proximal opening, a distal end having a distal opening, and a lumen between the proximal and distal openings, the lumen having a diameter large enough to slideably accommodate a standard guidewire; and
   an elongate shaft having no lumen, the elongate shaft being attached to the proximal end of the elongate tubular element,
   the mesh element being disposed on the elongate tubular element, and the mesh element being rotatable relative to the elongated tubular element when the mesh element is in the expanded configuration and no portion of the mesh element being in a fixed position relative to the elongate tubular member.

2. The device of claim 1, wherein the mesh element is slidable relative to the elongate tubular element when the mesh element is in the expanded configuration.

3. The device of claim 1, wherein the device further comprises a guidewire disposed within the lumen of the elongate tubular element.

4. The device of claim 3, wherein there are no stops on the guidewire.

5. The device of claim 1, wherein the lumen has a diameter of 0.025 cm to 0.097 cm.

6. The device of claim 1, wherein the lumen has a diameter of 0.064 cm±0.005 cm.

7. The device of claim 1, wherein the lumen has a diameter of 0.053 cm±0.005 cm.

8. The device of claim 1, wherein the lumen has a diameter of 0.043 cm±0.005 cm.

9. The device of claim 1, wherein the lumen has a diameter of 0.038 cm±0.005 cm.

10. The device of claim 1, wherein the lumen has a diameter of 0.029 cm±0.005 cm.

11. The device of claim 1, wherein the elongate tubular element has an outer diameter of 0.030 cm to 0.100 cm.

12. The device of claim 1, wherein the elongate tubular element has an outer diameter of 0.089 cm to 0.036 cm.

13. The device of claim 1, wherein the mesh element has an interior portion and a portion of the elongate tubular element is disposed within the interior portion.

14. The device of claim 1, wherein the mesh element has a shape in the expanded configuration which defines an interior portion having a proximal facing opening.

15. The device of claim 1, wherein the mesh element is self-expanding.

16. The device of claim 1, wherein the mesh element is self-contracting.

17. The device of claim 1, wherein the mesh element is actively expanded.

18. The device of claim 1, wherein the mesh element is actively contracted.

19. The device of claim 1, wherein the mesh element is attached to a proximal sliding band and a distal sliding band and the sliding bands are coupled to the elongate tubular element.

20. The device of claim 19, wherein a stop is disposed on the elongate tubular element between the proximal and distal sliding bands and the stop restricts translation of the mesh element along the elongate tubular element.

21. The device of claim 1, wherein the mesh element is attached to a distal sliding band and the mesh element is attached to a strut which is attached to a proximal sliding band and the sliding bands are coupled to the elongate tubular element.

22. The device of claim 21, wherein a stop is disposed on the elongate tubular element between the proximal and distal sliding bands and the stop restricts translation of the mesh element along the elongate tubular element.

23. The device of claim 1, wherein the shaft has a diameter of 0.025 cm to 0.097 cm.

24. The device of claim 1, wherein a medical device for treatment or diagnosis is carried on the shaft.

25. The device of claim 1, wherein the mesh element is a filter.

26. The device of claim 25, wherein the filter comprises braided metal strands.

27. The device of claim 25, wherein the filter comprises a polymer film with holes.

28. The device of claim 1, wherein the mesh element is fully occlusive.

29. The device of claim 1, wherein the elongate tubular element has a distal portion and a coil is disposed on the distal portion of the elongate tubular element.

30. The device of claim 1, wherein the length of the shaft and the elongate tubular element together is from 60 cm to 320 cm.

31. The device of claim 30, wherein the length of the elongate tubular element is from 5 to 75 cm.

32. The device of claim 30, wherein the length of the elongate tubular element is from 10 to 40 cm.

33. The device of claim 1, wherein the length of the shaft and the elongate tubular element together is from 135 cm to 185 cm.

34. The device of claim 1, wherein the length of the shaft and the elongate tubular element together is from 280 cm to 320 cm.

35. The device of claim 1, wherein the mesh element expands to establish at least line contact with substantially all of a lumenal cross section of a 2 mm to 35 mm vessel.

36. The device of claim 1, wherein the mesh element expands to establish at least line contact with substantially all of a lumenal cross section of a 2 mm to 5 mm vessel.

37. The device of claim 1, wherein the elongate tubular element has a longitudinal axis and the proximal opening of the elongate tubular element is oriented at an angle of from 5 degrees to 65 degrees to the longitudinal axis of the elongate tubular element.

38. The device of claim 1, wherein the elongate tubular element has a longitudinal axis and the proximal opening of the elongate tubular element is oriented at an angle of from 30 degrees to 105 degrees to the longitudinal axis of the elongate tubular element.

39. The device of claim 1, wherein the elongate tubular element has a distal end and a soft tip is attached to the distal end of the elongate tubular element.

40. The device of claim 1, wherein the elongate tubular element has a distal region that comprises slots.

41. The device of claim 1, wherein the elongate tubular element has a distal region that comprises removed regions.

42. The device of claim 1, wherein the elongate tubular element has a distal region that comprises a coil tip.

43. The device of claim 1, wherein the elongate tubular element has a distal region that comprises a composite tip.

44. The device of claim 1, the device further comprises a sheath disposed over a portion of the mesh element.

45. The device of claim 44, wherein the sheath comprises a proximal shaft and a tubular portion having a lumen.

46. The device of claim 44, wherein the sheath comprises a proximal hub and a tubular portion having a lumen.

47. The device of claim 44, wherein the sheath comprises a proximal shaft and a tubular portion having a lumen and a skive.

48. The device of claim 44, wherein the sheath comprises a proximal shaft and a tubular portion having a lumen and two skives.

49. An embolic protection device for removing emboli from a blood vessel in a patient's body, comprising:
- a mesh element being expandable from a collapsed configuration to an expanded configuration;
- an elongate tubular element having a proximal end having a proximal opening, a distal end having a distal opening, and a lumen between the proximal and distal openings, the lumen having a diameter large enough to slideably accommodate a standard guidewire; and
- an elongate shaft having no lumen, the elongate shaft being attached to the proximal end of the elongate tubular element,
- the mesh element being disposed on the elongate tubular element and the mesh element being attached to a proximal band and a distal band, the bands being coupled to the elongate tubular element, and one of the proximal and distal bands being fixed to the elongate tubular element and one of the proximal and distal bands being slidable on the elongate tubular element.

50. The device of claim 49, wherein an actuating wire or tube is attached to the slidable band.

51. The device of claim 49, wherein the proximal band is fixed and the distal band is slidable.

52. An embolic protection device for removing emboli from a blood vessel in a patient's body, comprising:
- a mesh element being expandable from a collapsed configuration to an expanded configuration;
- an elongate tubular element having a proximal end having a proximal opening, a distal end having a distal opening, and a lumen between the proximal and distal openings, the lumen having a diameter large enough to slideably accommodate a standard guidewire; and
- an elongate shaft having no lumen, the elongate shaft being attached to the proximal end of the elongate tubular element,
- the mesh element being disposed on the elongate tubular element and the mesh element being attached to a distal band and the mesh element being attached to a strut which is attached to a proximal band, the bands being coupled to the elongate tubular element, and one of the proximal and distal bands being fixed to the elongate tubular element and one of the proximal and distal bands being slidable on the elongate tubular element.

53. The device of claim 52, wherein an actuating wire or tube is attached to the slidable band.

54. The device of claim 52, wherein the proximal band is fixed and the distal band is slidable.

55. An embolic protection device for removing emboli from a blood vessel in a patient's body, comprising:
- a mesh element being expandable from a collapsed configuration to an expanded configuration; and
- an elongate tubular element having a proximal end having a proximal opening, a distal end having a distal opening, and a lumen between the proximal and distal openings, the lumen having a diameter large enough to slideably accommodate a standard guidewire,
- the mesh element being disposed on the elongate tubular element and the mesh element being rotatable relative to the elongate tubular element when the mesh element is in the expanded configuration, and no portion of the mesh element being in a fixed position relative to the elongate tubular member.

56. The device of claim 55, wherein the mesh element is slidable relative to the elongate tubular element when the mesh element is in the expanded configuration.

57. The device of claim 55, wherein the length of the elongate tubular element is from 60 to 320 cm.

58. The device of claim 55, wherein the device further comprises a guidewire disposed within the lumen of the elongate tubular element.

59. The device of claim 55, wherein the lumen has a diameter of 0.025 cm to 0.097 cm.

60. The device of claim 55, wherein the mesh element is a filter.

61. The device of claim 55, wherein the mesh element is fully occlusive.

62. An embolic protection device for removing emboli from a blood vessel in a patient's body, comprising:
- a mesh element being expandable from a collapsed configuration to an expanded configuration;
- a first elongate tubular element having a proximal end having a proximal opening, a distal end having a distal opening, and a lumen between the proximal and distal openings, the lumen having a diameter large enough to slideably accommodate a standard guidewire; and
- a second elongate tubular element having a proximal end having a proximal opening, a distal end having a distal opening, and a lumen between the proximal and distal openings, the lumen having a diameter large enough to slideably accommodate a standard guidewire,
- a distal region including the distal end of the second elongate tubular element being disposed in a portion of the lumen of the first elongate tubular element,
- a first portion of the mesh element being fixed to the first elongate tubular element and a second portion of the mesh element being fixed to the second elongate tubular element, the mesh element being expandable from a collapsed configuration to an expanded configuration by movement of the first and second elongate tubular elements relative to each other.

63. The device of claim 62, wherein the mesh element is expandable from a collapsed configuration to an expanded configuration by axial movement of the first and second elongate tubular elements relative to each other.

64. The device of claim 62, wherein the mesh element is expandable from a collapsed configuration to an expanded configuration by rotational movement of the first and second elongate tubular elements relative to each other.

65. The device of claim 62, wherein the length of the device is from 60 to 320 cm.

66. The device of claim 62, wherein the device further comprises a guidewire disposed within the lumens of the first and second elongate tubular elements.

67. The device of claim 62, wherein the lumens of the first and second elongate tubular elements each independently have diameters of 0.025 cm to 0.097 cm.

68. The device of claim 62, wherein the mesh element is a filter.

69. The device of claim 62, wherein the mesh element is fully occlusive.

70. A method for removing emboli from a blood vessel in a patient's body comprising:
- providing an embolic protection device comprising:

a mesh element being expandable from a collapsed configuration to an expanded configuration;

an elongate tubular element having a proximal end having a proximal opening, a distal end having a distal opening, and a lumen between the proximal and distal openings, the lumen having a diameter large enough to slideably accommodate a standard guidewire; and an elongate shaft having no lumen, the elongate shaft being attached to the proximal end of the elongate tubular element, and the mesh element being disposed on the elongate tubular element, and the mesh element being rotatable relative to the elongate tubular element when the mesh element is in the expanded configuration and no portion of the mesh element being in a fixed position relative to the elongate tubular member; and introducing the embolic protection device into a vessel in the patient's body.

71. The method of claim 70, further comprising advancing the embolic protection device through the vessel until the mesh element is positioned at a desired location distal to a treatment site and deploying the mesh element to its expanded configuration.

72. The method of claim 70, wherein the device further comprises a guidewire disposed within the lumen of the elongate tubular element.

73. The method of claim 72, wherein the guidewire is removed and replaced with a second guidewire.

74. The method of claim 70, wherein the lumen has a diameter of 0.025 cm to 0.097 cm.

75. The method of claim 70, wherein the device further comprises a sheath disposed over a portion of the mesh element.

76. The method of claim 75, further comprising advancing the embolic protection device through the vessel until the mesh element is positioned at a desired location distal to a treatment site and deploying the mesh element to its expanded configuration by removing the sheath from the mesh element.

77. The method of claim 70, wherein a guide catheter or guide lumen is advanced into the vessel in the patient's body to assist in introducing the embolic protection device.

78. The method of claim 70, wherein a recovery catheter is used to recover the embolic protection device.

79. The method of claim 70, further comprising advancing a medical device for diagnosis or treatment over the shaft.

* * * * *